United States Patent [19]

Beller et al.

[11] Patent Number: 5,360,924
[45] Date of Patent: Nov. 1, 1994

[54] PROCESS FOR PREPARING AROMATIC OLEFINS

[75] Inventors: Matthias Beller, Niedernhausen; Hartmut Fischer, Hofheim; Heinz Strutz, Usingen, all of Germany

[73] Assignee: Hoechst Aktiengesellschaft, Frankfurt am Main, Germany

[21] Appl. No.: 177,945

[22] Filed: Jan. 6, 1994

[30] Foreign Application Priority Data

Jan. 7, 1993 [DE] Germany .............................. 4300194

[51] Int. Cl.$^5$ ............................................ C07C 69/76
[52] U.S. Cl. ........................................ 560/55; 560/20; 560/51; 560/53; 560/104; 560/434; 560/465; 560/495; 564/161; 564/163; 564/166; 564/182; 558/415; 558/418
[58] Field of Search ................ 560/104, 55, 20, 53, 560/51; 562/434, 465, 495; 558/415, 418; 564/161, 163, 166, 182

[56] References Cited

FOREIGN PATENT DOCUMENTS 508264 10/1992 European Pat. Off. .
1301996 1/1973 United Kingdom .

OTHER PUBLICATIONS

Kikukawa, K et al Chem. Lett 1977 p. 159.
Chem. Abst. 109, 92408 1988.
Bulletin of the Chemical Society of Japan, Band 52, Nr. 9, 1979 pp. 2609–2610.
Tetrahedron, Band 37, 1981, pp. 31–36.
Chemistry Letters, Nr. 1, 1977, pp. 159–162.

*Primary Examiner*—Paul J. Killos

[57] ABSTRACT

Process for preparing aromatic olefins of the formula (1)

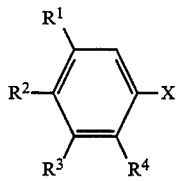

in which $R^1$–$R^3$ are hydrogen, alkyl ($C_1$–$C_8$), alkoxy-($C_1$–$C_5$), phenyl, fluorine, chlorine, bromine, —OH, —$NO_2$, —CN, —CHO, —COalkyl($C_1$–$C_4$), —COphenyl, —COOalkyl ($C_1$–$C_4$), —OCOalkyl($C_1$–$C_4$), —NHCOalkyl($C_1$–$C_4$), —$CF_3$, —$NH_2$, —NH—alkyl(-$C_1$–$C_4$) or —N(alkyl($C_1$–$C_4$))$_2$ and $R^4$ is hydrogen, alkyl($C_1$–$C_8$), phenyl, fluorine, chlorine, bromine, —OH, —$NO_2$, —CN, —CHO or —OCOalkyl ($C_1$–$C_4$), and X is, inter alia, alkenyl($C_2$–$C_{12}$) or cycloalkenyl($C_4$–$C_8$) or the group

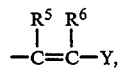

in which $R^5$ and $R^6$ are, independently of one another, hydrogen or methyl, and Y is —phenyl, —CN, —COOH, —COOalkyl($C_1$–$C_{12}$), —COOphenyl,

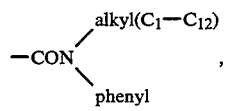

—CON (phenyl)$_2$, —COalkyl($C_1$–$C_{12}$), —COphenyl, —Oalkyl($C_1$–$C_{12}$), —Ophenyl or the radical

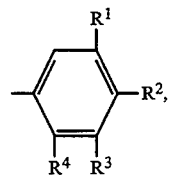

(Abstract continued on next page.)

in which $R^1$–$R^4$ are as defined above, by reacting an aryldiazonium salt of the formula (2)
in which $R^1$–$R^4$ are as defined and Z is the equivalent of an anion of an acid having a p$K_a$ of less than 7, with an olefin of the formula (3)
16 Claims, No Drawings

PROCESS FOR PREPARING AROMATIC OLEFINS

The invention relates to an improved process for preparing aromatic olefins by catalyzed olefination of the corresponding aryldiazonium salts in the presence of heterogeneous palladium catalysts.

The preparation of aromatic olefins by catalyzed olefination of aryldiazonium salts in the presence of a homogeneous palladium catalyst is a relatively new synthetic method. For application in industry, however, the processes hitherto described in the literature for preparing aromatic olefins from diazonium salts in the presence of a catalyst are unsuitable because of the lack of an effective method for catalyst recovery.

K. Kikukawa et al. (Chem. Lett., 1977, 159; Bull. Chem. Soc., 1979, 52, 2609; Tetrahedron, 1981, 37, 31) describe the vinylation of aryldiazonium salts in the presence of homogeneous palladium(O) complexes and a base. The reactions described therein only give good yields when the particularly expensive bisbenzylidenepalladium(0) is used as catalyst in the presence of a stoichiometric excess of base. In addition, relatively large amounts of the palladium complex are used (2 mol %, based on aryldiazonium salt), which must be discarded after the reaction.

According to W. Yong et al. (Synthesis, 1991, 967), the reaction of aryldiazonium salts with camphene in the presence of palladium acetate in ethanol mostly gives only moderate yields. This reaction is unsuitable for an industrial synthesis since it uses palladium acetate as catalyst, which requires complicated purification after the reaction before it can be be re-used. The reaction has hitherto only been described for camphene.

According to J. H. Xu et al. (Youji Huaxue, 1987, 452; C.A.,1988, 109, 92408), aryldiazonium salts can also be reacted with acrylic acid and acrylic esters with lithium tetrachloropalladate as catalyst in methanol. In this process too, recycling of the catalyst is technically very complicated.

EP-A 0 508 264 relates to a process for preparing arylolefins by reaction of aryldiazonium salts with olefins in the presence of a palladium catalyst. Although the use of heterogeneous palladium catalysts is mentioned (cf. EP-A 0 508 264 A1 page 4, lines 2 to 3), it is experimentally verified in only one case, namely the reaction of aniline-2-sulfonic acid with ethylene to give styrene-2-sulfonic acid (Example 6). However, as shown by comparison with Example 4 carried out using Pd(OAc)$_2$, the yield decreases considerably when using a supported palladium catalyst (10% Pd on carbon) (Example 4: 87% yield; Example 7: 74% yield). In both examples the reaction is carried out with the addition of a base which is used in excess based on the aniline-2-sulfonic acid. As the experimental finding proves (see comparative experiment in the experimental section), the method practiced in the examples of EP-A 0 508 264, of preparing the aryldiazonium salts in situ and subsequently processing further, cannot be generally applied to the use of palladium-containing supported catalysts. The comparative experiment verifies that the desired aromatic olefin is not formed even in small amounts.

There was therefore a considerable need for a general process for the catalytic olefination of aryldiazonium salts which gives aromatic olefins, in particular cinnamic acids and their derivatives and also styrenes and stilbenes, in as high a yield as possible without interfering impurities and in a simple manner, and which additionally allows a simple industrial synthesis. In particular, the aim was to find a method which uses a simple stable catalyst system which is industrially recoverable but still has a similar activity to conventional homogeneous palladium catalysts.

It has now been found, surprisingly, that aromatic olefins of the formula I

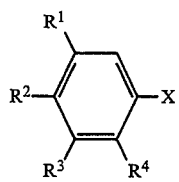

(1)

in which $R^1$, $R^2$ and $R^3$ are, independently of one another, hydrogen, alkyl (C$_1$-C$_8$), alkoxy(C$_1$-C$_5$), phenyl, fluorine, chlorine, bromine, —OH, —NO$_2$, —CN, —CHO, —COalkyl (C$_1$-C$_4$), alkyl—COphenyl, —COOalkyl (C$_1$-C$_4$), —OCOalkyl (C$_1$-C$_4$), —NHCO—CF$_3$, —NH$_2$, —NH alkyl (C$_1$-C$_4$) or —N(alkyl-(C$_1$-C$_4$))$_2$ and $R^4$ is hydrogen, alkyl(C$_1$-C$_8$), phenyl, fluorine, chlorine, bromine, —OH, —NO$_2$, —CN, —CHO or —O-COalkyl (C$_1$-C$_4$), where the alkyl and the alkoxy groups may be straight-chain or branched, and X is alkenyl(C$_2$-C$_{12}$), cycloalkenyl(C$_4$-C$_8$) or the group

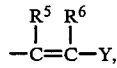

in which $R^5$ and $R^6$ are, independently of one another, hydrogen or methyl, and Y is —phenyl, —CN, —COOH, —COOalkyl (C$_1$-C$_{12}$), —COOphenyl,

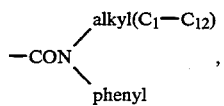

or the radical

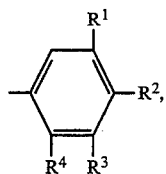

in which $R^1$—$R^4$ are as defined above, can be prepared in an advantageous manner by reacting an aryldiazonium salt of the formula (2)

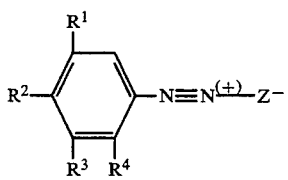

(2)

in which $R^1$, $R^2$, $R^3$ and $R^4$ are as defined above and Z is the equivalent of an anion of an organic or inorganic acid having a $pK_a$ of less than 7, with an olefin of the formula (3)

$$HX \quad (3)$$

in which X is as defined above, in the presence of catalytic amounts of a heterogeneous palladium catalyst in an organic solvent at temperatures from about −20° C. to about 150° C., preferably from about 0° C. to about 100° C.

Aryldiazonium salts are taken to mean aryldiazonium salts as such, particularly in pure form, for example in a crystalline state, but not prepared in situ.

If X in the above formula (3) is an alkenyl($C_3$–$C_2$) or cycloalkenyl($C_4$–$C_8$) group the reaction can result in a shift of the double bond, which generally produces mixtures of isomers.

With respect to the meaning of $R^5$ and $R^6$, it is advantageous if at least one of the radicals $R^5$ and $R^6$ is a hydrogen atom.

The substituents $R^1$, $R^2$, R3 and $R^4$ can, for example, be a methyl, ethyl, n-propyl, isopropyl, n-butyl, sec-butyl, t-butyl, n-pentyl, 2-pentyl, n-hexyl, n-heptyl, n-octyl or n-decyl group, also a methoxy, ethoxy, n-propoxy, isopropoxy, n-butoxy, n-pentyloxy, hexyloxy, octyloxy, decyloxy or dodecyloxy group, also a carboxymethyl, -ethyl, -n-propyl, -isopropyl, -n-butyl or -sec-butyl group, otherwise an acetamide, propionamide, butyramide or valeramide group, also an N,N-dimethylamino, N,N-diethylamino, N,N-di-n-propylamino, N,N-di-n-butylamino, N-methyl-N-ethylamino or N-methyl-N-n-propylamino group, finally an acetoxy, propionyloxy or butyryloxy group.

The alkyl groups contained in the groups Y are preferably methyl, ethyl, n-butyl or 2-ethylhexyl groups.

The alkyl groups for $R^1$–$R^3$ are preferably straight-chain and preferably contain 1–4, particularly preferably 1–2, carbon atoms. The preferred alkoxy groups for $R^1$–$R^3$ are the methoxy and ethoxy groups.

The compounds of the stated formula (2) which are preferably used are ones in which $R^4$ is hydrogen and $R^1$ to $R^3$ are, independently of one another, hydrogen, phenyl, alkyl ($C_1$—$C_3$), in particular methyl, methoxy, ethoxy, acetoxy, —$NO_2$, —CN, —CHO, —Cl, —NH-COalkyl ($C_1$—$C_2$), —COO—alkyl ($C_1$—$C_2$), —COalkyl ($C_1$—$C_2$), —CO—phenyl or —N(alkyl—($C_1$—$C_2$))$_2$.

Particular preference is given to using compounds of the formula (2) in which $R^1$, $R^3$ and $R^4$ are hydrogen or methyl and $R^2$ is hydrogen, methyl, phenyl, methoxy, ethoxy, acetoxy, —CN, —$NO_2$, —COOalkyl ($C_1$–$C_2$), —CHO, —Cl or —$COCH_3$.

Compounds of the stated formula (3) which are preferably used are ones in which X is alkenyl($C_2$–$C_8$), cyclopentenyl or cyclohexenyl or the group

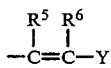

in which one of the substituents $R^5$ and $R^6$ is a hydrogen atom and the other is a methyl group, or both are each a hydrogen atom, and Y is phenyl, —CN, —CON(phenyl)$_2$, —COOH, —$CONH_2$,

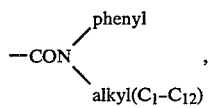

but in particular $CO_2$-methyl, $CO_2$-ethyl, $CO_2$-2-ethylhexyl.

Particular preference is given to styrene, ethylene, propylene, methyl acrylate, ethyl acrylate, butyl acrylate or 2-ethylhexyl acrylate as compounds of the stated formula (3).

Most preferred is the preparation of butyl or 2-ethylhexyl esters of 4-methoxy-, 4-acetyl-, 4-formyl-, 4-nitro- and 4-cyanocinnamic acids by reaction of 4-methoxy-, 4-acetyl-, 4-formyl-, 4-nitro- or 4-cyanobenzenediazonium salt with the corresponding acrylic ester, and also the preparation of 4-cyanostilbene or 4,4′-dicyanostilbene by reaction of 4-cyanobenzenediazonium salt with styrene or ethylene, respectively.

The palladium catalyst is advantageously used on a support material, such as activated carbon, calcium carbonate, barium sulfate, pumice, alumina, kieselguhr, silica gel and/or aluminum oxide. Palladium is preferably used applied to activated carbon or aluminum oxide as support material.

It is advantageous to use a supported palladium catalyst which contains from about 1 to about 20% by weight, preferably from about 2 to about 10% by weight, of palladium, based on the support material.

With respect to the ratio of palladium to aryldiazonium salt it is advantageous to use from about 0.001 to about 20 mol %, preferably from about 0.1 to about 1 mol %, of palladium, based on the aryldiazonium salt.

As far as the ratio of the reactants is concerned, it is advantageous to react 1 mol of aryldiazonium salt of the formula (2) with from about 0.2 to about 10 mol, preferably from about 0.4 to about 5 mol, particularly preferably from about 0.6 to about 4 mol, of olefin of the formula (3).

Possible acid radicals Z are, for example, $BF_4^-$, $HSO_4^-$, $PF_6^-$, $SO_4^{2-}$, $Cl^-$, $CH_3COO^-$ and aryl-$SO_3^-$ in which the aryl radical may be substituted, for example naphthalenesulfonate or benzenesulfonate.

As far as the industrial utility of the compounds obtainable according to the process is concerned, stilbenes are used as optical brighteners, and cinnamic esters are used, for example, as UV absorbers in cosmetics. Styrenes are suitable for the production of polymers. Aromatic olefins are also particularly suitable for the preparation of pharmaceuticals, herbicide, fungicides and fragrances.

The processes known hitherto for olefination of aryldiazonium salts generally use homogeneous palladium catalysts. The comparable olefination of aryl bromides and aryl chlorides is likewise carried out with homogeneous palladium compounds. In some cases, a reaction is also achieved with selected heterogeneous palladium catalysts. However, the yields are usually lower than with homogeneous catalysts; in many cases the reaction does not occur at all. It was therefore surprising that in the process of the invention heterogeneous palladium catalysts can be used as effectively as homogeneous palladium compounds.

The simplified process of the invention has the following advantages:

It provides a simple general method which allows aryldiazonium salts to be reacted with olefins in such a way that aromatic olefins can be obtained industrially more readily than hitherto. A significant advantage is that the catalyst system is present in heterogeneous form and thus recycling of the valuable palladium catalyst is possible by simple filtration. A further advantage is that the addition of bases can be avoided and thereby no salt waste is obtained, which is ecologically favorable.

The following examples serve to illustrate the process of the invention, without representing a limitation.

EXAMPLE 1

7.0 g (31.5 mmol) of p-methoxybenzenediazonium tetrafluoroborate and 6.3 g (63.0 mmol) of ethyl acrylate were suspended in 40 ml of ethanol (98% strength). The suspension obtained was admixed with 0.325 g (0.16 mmol) of palladium on activated carbon (5% Pd content) at 0° C. The reaction mixture was then heated to 60° C. over a period of one hour and stirred at this temperature for 12 hours. After cooling to room temperature, the catalyst was filtered off and washed with ethanol. Subsequently the filtrate was diluted with 100 ml of dichloromethane and washed three times with 60 ml of water. The organic phase was concentrated in vacuo, resulting in 8.0 g of crude product which, according to GC and NMR spectroscopic analyses, contained 85% of ethyl p-methoxycinnamate.

Yield: 98% (of theoretical) of ethyl p-methoxycinnamate

EXAMPLE 2

The method was as in Example 1, but using 1 mol % of palladium on aluminum oxide (5% Pd content) as catalyst system.

Yield: 89% (of theoretical) of ethyl p-methoxycinnamate

EXAMPLE 3

The method was as in Example 1, but using 1 mol % of palladium on barium sulfate (5% Pd content) as catalyst system.

Yield: 94% (of theoretical) of ethyl p-methoxycinnamate

EXAMPLE 4

The method was as in Example 1, but using 1 mol % of palladium on activated carbon (5% Pd content) as catalyst system. The starting compounds were 7.0 g (31.5 mmol) of p-methoxybenzenediazonium tetrafluoroborate and 4.5 g (63.0 mmol) of acrylic acid suspended in 40 ml of methanol.

Yield: 72% (of theoretical) of methyl p-methoxycinnamate

EXAMPLE 5

The method was as in Example 1, but using 1 mol % of palladium on activated carbon (5% Pd content) as catalyst. The starting compounds were 7.0 g (31.5 mmol) of p-methoxybenzenediazonium tetrafluoroborate and 5.4 g (63.0 mmol) of methyl acrylate suspended in 40 ml of methanol.

Yield: 95% (of theoretical) of methyl p-methoxycinnamate

EXAMPLE 6

The method was as in Example 1, but using 1 mol % of palladium on activated carbon (5% Pd content) as catalyst. The starting compounds were 6.5 g (31.5 mmol) of 3-methylbenzenediazonium tetrafluoroborate and 6.3 g (63.0 mmol) of ethyl acrylate suspended in 40 ml of ethanol.

Yield: 89% (of theoretical) of ethyl 3-methylcinnamate

EXAMPLE 7

The method was as in Example 1, but using 1 mol % of palladium on activated carbon (5% Pd content) as catalyst. The starting compounds were 7.1 g (31.5 mmol) of 4-chlorobenzenediazonium tetrafluoroborate and 6.3 g (63 mmol) of ethyl acrylate suspended in 40 ml of ethanol.

Yield: 92% (of theoretical) of ethyl 4-chlorocinnamate

EXAMPLE 8

7.0 g (31.5 mmol) of p-methoxybenzenediazonium tetrafluoroborate and 11.61 g (63.0 mmol) of 2-ethylhexyl acrylate are suspended in 40 ml of dimethyl sulfoxide and admixed with 0.75 g (0.32 mmol) of palladium on activated carbon (5% Pd content) at 0° C. The reaction mixture was then heated to 60° C. over a period of one hour and stirred at this temperature for 12 hours. After cooling to room temperature, the catalyst was filtered off and washed with ethanol. Subsequently the filtrate was diluted with 100 ml of dichloromethane and washed three times with 60 ml of water. The organic phase was concentrated in vacuo. The crude product obtained was subjected to column chromatography.

Yield: 80% of 2-ethylhexyl p-methoxycinnamate

COMPARATIVE EXPERIMENT 12.3 g of 4-anisidine (4-methoxyaniline) are mixed while stirring with 10 ml of concentrated sulphuric acid and 60 ml of 2-ethylhexanol and the mixture is cooled to about 10° C. Subsequently 11.7 g of amyl nitrite are added and after addition is complete the mixture is stirred for a further 40 minutes. The reaction mixture is subsequently admixed with 20.2 g of 2-ethylhexyl acrylate and 100 mg of Pd (5% Pd on activated carbon) and heated to 65° C. over a period of 1 hour and stirred for a further 12 hours at this temperature. The mixture is diluted with 100 ml of water and extracted with 200 ml of dichloromethane. As examination by thin-layer chromatography and gas chromatography shows, 2-ethylhexyl p-methoxycinnamate has not been formed in even the smallest amounts. The 2-ethylhexyl acrylate employed is essentially present in unchanged form.

What is claimed is:

1. A process for preparing aromatic olefins of the formula I

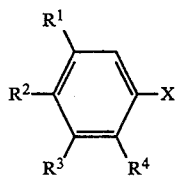

(1)

in which $R^1$, $R^2$ and $R^3$ are, independently of one another, hydrogen, alkyl($C_1$–$C_8$), alkoxy($C_1$–$C_5$), phenyl, fluorine, chlorine, bromine, —OH, —NO$_2$, —CN, —CHO, —COalkyl(C$_1$-C$_4$), —COphenyl, —COOalkyl(C$_1$-C$_4$) —OCOalkyl(C$_1$-C$_4$), —NHCO—alkyl(-C$_1$-C$_4$), —CF$_3$, NH$_2$, —NHalkyl(C$_1$-C$_4$) or -N(alkyl-(C$_1$-C$_4$))$_2$ and R$^4$ is hydrogen, alkyl(C$_1$-C$_8$), phenyl, fluorine, chlorine, bromine, —OH, —NO$_2$, —CN, —CHO or -OCOalkyl (C$_1$-C$_4$), where the alkyl and the alkoxy groups are straight-chain or branched, and X is alkenyl(C$_2$-C$_2$), cycloalkenyl(C$_4$-C$_8$) or the group

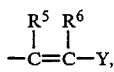

in which R$^5$ and R$^6$ are, independently of one another, hydrogen or methyl, and Y is -phenyl, —CN, —COOH, —COOalkyl(C$_1$-C$_{12}$), —COOphenyl, —CON(alkyl(C$_1$-C$_{12}$))$_2$,—CONHalkyl(C$_1$-C$_{12}$), —CON

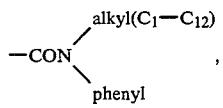

—CON(phenyl)$_2$, —COalkyl(C$_1$-C$_{12}$), —COphenyl, —Oalkyl(C$_1$-C$_{12}$), —Ophenyl or the radical

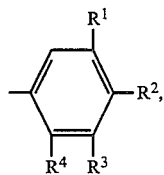

in which R$^1$-R$^4$ are as defined above, which comprises reacting an aryldiazonium salt of the formula (2)

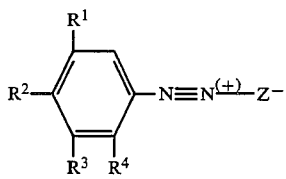

in which R$^1$, R$^2$, R$^3$ and R$^4$ are as defined above and Z is the equivalent of an anion of an organic or inorganic acid having a pK$_a$ of less than 7, with an olefin of the formula (3)

HX                                                          (3)

in which X is as defined above, in the presence of catalytic amounts of a heterogeneous palladium catalyst in an organic solvent at temperatures from about −20° C. to about 150° C.

2. The process as claimed in claim 1, wherein the reaction is carried out at temperatures from about 0° C. to about 100° C.

3. The process as claimed in claim 1, wherein the support material of the heterogeneous palladium catalyst comprises activated carbon, aluminum oxide, barium sulfate, pumice, alumina, kieselguhr or silica gel.

4. The process as claimed in claim 1, wherein the support material of the heterogeneous palladium catalyst comprises activated carbon, aluminium oxide or barium sulphate.

5. The process as claimed in claim 1, wherein the heterogeneous palladiumcatalyst used contains from about 1 to about 20% by weight of palladium, based on the support material.

6. The process as claimed in claim 1, wherein the heterogeneous palladiumcatalyst used contains from about 2 to about 10% by weight of palladium, based on the support material.

7. The process as claimed in claim 1, wherein from about 0.001 to about 20 mol % of palladium, based on the aryldiazonium salt, is used.

8. The process as claimed in claim 1, wherein from about 0.1 to about 1 mol % of palladium, based on the aryldiazonium salt, is used.

9. The process as claimed in claim 1, wherein about 1 mol of aryldiazonium salt is reacted with from about 0.2 to about 10 mol of olefin.

10. The process as claimed in claim 1, wherein about 1 mol of aryldiazonium salt is reacted with from about 0.4 to about 5 mol of olefin.

11. The process as claimed in claim 1, wherein about 1 mol of aryldiazonium salt is reacted with from about 0.6 to about 4 mol of olefin.

12. The process as claimed in claim 1, wherein, in said olefin of formula (3), X is the group

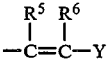

and wherein at least one of the radicals R$^5$ and R$^6$ is a hydrogen atom and Y is a COOH, COOmethyl, COOethyl, COOpropyl, COObutyl or COO-2-ethylhexyl group.

13. The process as claimed in claim 1, wherein, in said olefin of formula (3), X is an alkenyl(C$_2$-C$_8$), cyclopentenyl or cyclohexenyl group.

14. The process as claimed in claim 1, wherein the compound of the formula (3) specified in claim 1 is styrene, ethylene, propylene, methyl acrylate, ethyl acrylate, propyl acrylate, butyl acrylate or 2-ethylhexyl acrylate and is reacted with 4-methoxy-, 4-acetyl-, 4-formyl-, 4-nitro- or 4-cyanobenzenediazonium salt.

15. The process as claimed in claim 1, wherein the compound of the formula (3) specified in claim 1 is styrene or ethylene and is reacted with 4-cyanobenzenediazonium salt.

16. The process as claimed in claim 1, wherein, in said aryldiazonium salt of formula (2), Z is BF$_4^-$, HSO$_4^-$, PF$_6^-$, Cl$^-$, SO$_4^{2-}$, CH$_3$COO$^-$ or aryl-SO$_3^-$ in which the aryl radical may be substituted.

* * * * *

UNITED STATES PATENT AND TRADEMARK OFFICE
CERTIFICATE OF CORRECTION

PATENT NO. : 5,360,924
DATED : November 1, 1994
INVENTOR(S) : Matthias Beller, et al It is certified that error appears in the above-indentified patent and that said Letters Patent is hereby corrected as shown below:

In claim 1, column 7, line 4 "$NH_2$" should read -- $-NH_2$ --;

at column 7, line 10 "$C_2-C_2$" should read -- $C_2-C_{12}$ --;

at column 7, at the end of line 22 "—CON" should be deleted;

at column 7, line 30 should begin with -- —$CONH_2$, --

In claim 5, column 8, line 13, --palladiumcatalyst-- should read --palladium catalyst--.

In claim 6, column 8, line 17, --palladiumcatalyst-- should read --palladium catalyst--.

Signed and Sealed this

Eighth Day of August, 1995

Attest:

BRUCE LEHMAN

*Attesting Officer*  *Commissioner of Patents and Trademarks*